US006395270B1

(12) United States Patent
Carlson et al.

(10) Patent No.: US 6,395,270 B1
(45) Date of Patent: *May 28, 2002

(54) ACTIVATED PROTEIN C FORMULATIONS

(75) Inventors: Andrew David Carlson; Theodore Arsay Sheliga, both of Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/662,232

(22) Filed: Sep. 14, 2000

Related U.S. Application Data

(63) Continuation of application No. 09/065,975, filed on Apr. 24, 1998, now Pat. No. 6,159,468.
(60) Provisional application No. 60/045,255, filed on Apr. 28, 1997.

(51) Int. Cl.[7] ............................. A61K 38/48; C12N 9/50
(52) U.S. Cl. ..................................... 424/94.64; 435/219
(58) Field of Search ........................ 424/94.64; 435/219

(56) References Cited

U.S. PATENT DOCUMENTS

| | | | |
|---|---|---|---|
| 4,775,624 A | 10/1988 | Bang et al. | 435/226 |
| 4,849,403 A | 7/1989 | Stocker et al. | 514/2 |
| 4,877,608 A | 10/1989 | Lee et al. | 424/176.1 |
| 4,981,952 A | 1/1991 | Yan | 530/384 |
| 4,992,373 A | 2/1991 | Bang et al. | 435/226 |
| 5,084,273 A | 1/1992 | Hirahara | 424/94.6 |
| 5,093,117 A | 3/1992 | Lawrence et al. | 424/1.49 |
| 5,112,949 A | 5/1992 | Vukovich | 530/380 |
| 5,175,087 A | 12/1992 | Ranby et al. | 435/13 |
| 5,395,923 A | 3/1995 | Bui-Khac et al. | 530/381 |
| 5,413,732 A | 5/1995 | Buhl et al. | 252/182.11 |
| 5,442,064 A | 8/1995 | Pieper et al. | 544/360 |
| 5,453,373 A | 9/1995 | Gerlitz et al. | 435/240.2 |
| 5,478,558 A | 12/1995 | Eibl et al. | 424/94.63 |
| 5,516,650 A | 5/1996 | Foster et al. | 435/68.1 |
| 5,831,025 A | 11/1998 | Ogata et al. | 530/380 |
| 5,962,299 A | * 10/1999 | Miyata et al. | |
| 6,008,199 A | 12/1999 | Grinnell et al. | |
| 6,159,468 A | 12/2000 | Carlson et al. | 424/94.64 |
| 6,162,629 A | 12/2000 | Baker et al. | 435/212 |

FOREIGN PATENT DOCUMENTS

| | | |
|---|---|---|
| DE | 3823519 | 1/1990 |
| EP | 314095 | 5/1989 |
| EP | 326014 | 8/1989 |
| EP | 0314095 B1 | 12/1992 |
| EP | 662513 | 7/1995 |
| EP | 0315968 B2 | 4/1997 |
| EP | 0 445 939 B1 | 5/1997 |
| EP | 0726076 B1 | 8/2000 |
| JP | 01 226900 | 9/1989 |
| JP | 07 165605 | 6/1995 |
| JP | 08301786 | 11/1996 |
| WO | WO 91/12320 | 8/1991 |
| WO | 95/11966 | 5/1995 |
| WO | Wo 97/20043 A1 | 6/1997 |
| WO | 98/48818 | 11/1998 |

OTHER PUBLICATIONS

Yu–Chang, J.W. and Hanson MA (1988) "Parenteral Formualtions of Proteins and Peptides: Stability and Stabilizers" *Journal of Parenteral Science and Technology* 42(Supp): S3–S26.
S. A. Steiner, et al. "Stimulation of the Amidase and Esterase Activity of Activated Bovine Plasma Protein C by Monovalent Cations" *Biochemical and Biophysical Research Communications* 94(1) :340–347 (May 14, 1980).
Esmon, C.T., "The Regulation of Natural Anticoagulant Pathways" *Science*, vol. 235, pp. 1348–1352 (Mar. 1987).
Grinnell, et al., "Trans–Activated Expression of Fully Gamma–Carboxylated Recombinant Human Protein C, An Antithrombotic Factor", *Bio/Technology* 5:1189–1192, 1987.

* cited by examiner

*Primary Examiner*—Jon P. Weber
(74) *Attorney, Agent, or Firm*—Brian P. Barrett; Steven P. Caltrider

(57) ABSTRACT

The present invention relates to pharmaceutical formulations of activated protein C which also comprises sucrose, sodium chloride and sodium citrate buffer at a pH between about 5.5 and about 6.5. The activated protein C formulations of the present invention are more stable than other formulations of activated protein C and demonstrate fewer degradation products over time.

43 Claims, No Drawings

ACTIVATED PROTEIN C FORMULATIONS

This application is a continuation of U.S. patent application Ser. No. 09/065,975, filed Apr. 24, 1998, now U.S. Pat. No. 6,159,468.

This application claims the benefit of U.S. Provisional Application No. 60/045,255, filed April 28, 1997.

FIELD OF THE INVENTION

This invention is in the field of human medicine, particularly in the treatment of vascular disorders with activated protein C. More specifically, the present invention relates to formulations of activated human protein C.

BACKGROUND OF THE INVENTION

Protein C is a serine protease and naturally occurring anticoagulant that plays a role in the regulation of homeostasis by inactivating Factors $V_a$ and $VIII_a$ in the coagulation cascade. Human protein C is made in vivo primarily in the liver as a single polypeptide of 461 amino acids. This single chain precursor molecule undergoes multiple post-translational modifications including 1) cleavage of a 42 amino acid signal sequence; 2) proteolytic removal from the one chain zymogen of the lysine residue at position 156 and the arginine residue at position 157 to make a 2-chain zymogen form of the molecule, (i.e., a light chain of 155 amino acid residues attached through a disulfide bridge to the serine protease-containing heavy chain of 262 amino acid residues); 3) vitamin K-dependent carboxylation of nine glutamic acid residues clustered in the first 42 amino acids of the light chain, resulting in nine gamma-carboxyglutamic acid residues; and 4) carbohydrate attachment at four sites (one in the light chain and three in the heavy chain). The heavy chain contains the well established serine protease triad of Asp 257, His 211 and Ser 360. Finally, the circulating 2-chain zymogen is activated in vivo by thrombin at a phospholipid surface in the presence of calcium ion. Activation results from removal of a dodecapeptide at the N-terminus of the heavy chain, producing activated protein C (aPC) possessing enzymatic activity.

In addition to the enzymatic activities of aPC within the blood coagulation cascade, aPC also can autodegrade, leading to decreased functionality as an anticoagulant. Applicants have discovered an important degradation pathway. Autodegradation of the N-terminus of the light chain may result in a clip on either side of the histidine residue at position 10. Thus, this degradation pathway yields two inactive products: 1) des(1–9) activated protein C, wherein the first nine N-terminal residues of the light chain have been removed; and 2) des(1–10) activated protein C, wherein the first ten N-terminal residues of the light chain have been removed. This degradation pathway, which has not been previously reported, results in loss of anticoagulant activity due to the removal of the critical GLA residues at positions 6 and 7. Therefore, minimizing the level of the des(1–9) and des(1–10) activated Protein C autodegradation products is important in achieving a potent, high purity, activated protein C pharmaceutical formulation. These variants were previously unknown degradation products and are exceedingly difficult, if not impossible, to remove by conventional purification techniques. Applicants have further discovered that solid-state solubility is significantly enhanced in the presence of a select group of bulking agents.

It is clearly desirable to minimize such degradation of activated protein C in both the solution and lyophilized solid states. Accordingly, these discoveries allow the preparation of potent, high purity, activated protein C formulations which are pharmaceutically elegant to the health care provider.

The present invention provides improved formulations of activated protein C substantially free of such autodegradation products, particularly, des(1–9) and des(1–10) forms of the light chain of activated protein C. Therefore, said formulations are suitable for administration to a patient in need thereof.

SUMMARY OF THE INVENTION

The present invention provides a stable lyophilized formulation comprising activated protein C and a bulking agent selected from the group consisting of mannitol, trehalose, raffinose, sucrose, and mixtures thereof.

The present invention also provides a stable lyophilized formulation comprising about 2.5 mg/mL activated protein C, about 15 mg/mL sucrose, and about 20 mg/mL NaCl. Furthermore, the present invention provides a stable lyophilized formulation comprising about 5 mg/mL activated protein C, about 30 mg/mL sucrose, and about 38 mg/mL NaCl.

The present invention also provides a process for preparing a formulation comprising activated protein C and a bulking agent selected from the group consisting of mannitol, trehalose, raffinose, and sucrose and mixtures thereof.

The invention also provides a unit dosage form comprising a unit dosage receptacle containing the formulation wherein the weight to weight ratio is about 1 part activated protein C, about 7.6 parts salt and about 6 parts bulking agent.

The invention further provides a method of treating disease states involving intravascular coagulation comprising the administration of a formulation of activated protein C described herein.

DETAILED DESCRIPTION OF THE INVENTION

For purposes of the present invention, as disclosed and claimed herein, the following terms are as defined below.

aPC or activated protein C refers to activated protein C whether recombinant or plasma derived. aPC includes and is preferably human activated protein C although aPC may also include other species or derivatives having protein C proteolytic, amidolytic, esterolytic, and biological (anticoagulant or pro-fibrinolytic) activities. Examples of protein C derivatives are described by Gerlitz, et al., U.S. Pat. No. 5,453,373, and Foster, et al., U.S. Pat. No. 5,516,650, the entire teachings of which are hereby incorporated by reference.

APTT—activated partial thromboplastin time.

r-hPC—recombinant human protein C zymogen.

r-aPC—recombinant activated protein C produced by activating protein C zymogen in vitro or in vivo or by direct secretion of the activated form of protein C from procaryotic cells, eukaryotic cells, or transgenic animals including, for example, secretion from human kidney 293 cells as a zymogen then purified and activated by techniques well known to the skilled artisan and demonstrated in Yan, U.S. Pat. No. 4,981,952, and Cottingham, WO 97/20043, the entire teachings of which are herein incorporated by reference.

Continuous infusion—continuing substantially uninterrupted the introduction of a solution into a blood vessel for a specified period of time.

Bolus injection—the injection of a drug in a defined quantity (called a bolus) at once.

Suitable for administration—a lyophilized formulation or solution that is appropriate to be given as a therapeutic agent.

Zymogen—protein C zymogen, as used herein, refers to secreted, inactive forms, whether one chain or two chains, of protein C.

Pharmaceutically acceptable buffer—a pharmaceutically acceptable buffer is known in the art. Pharmaceutically acceptable buffers include sodium phosphate, sodium citrate, sodium acetate, or TRIS.

Activated protein C is an antithrombotic agent with a wider therapeutic index than available anticoagulants, such as heparin and the oral hydroxycoumarin type anticoagulants. As an antithrombotic agent, aPC has a profound effect on the treatment of a wide variety of acquired disease states involving intravascular coagulation, including thrombotic stroke, deep vein thrombosis, pulmonary embolism, peripheral arterial thrombosis, emboli originating from the heart or peripheral arteries, acute myocardial infarction, disseminated intravascular coagulation, and acute pre or postcapillary occlusions, including transplantations or retina thrombosis.

The present invention relates to formulations of activated protein C. The desired formulation would be one that is a stable lyophilized product of high purity consisting of activated protein C and a bulking agent selected from the group consisting of mannitol, trehalose, raffinose, and sucrose. The lyophilized product is reconstituted with the appropriate diluent such as sterile water or sterile saline. Preferably, the resulting solution has a pH of about 5.5 to about 6.5.

The molecular interactions in a formulation between activated protein C, buffer, salt concentration, pH, temperature, and bulking agents, are complex, and the role that each factor contributes to the stability of the formulation is unpredictable. The lyophilized formulations of the present invention provide stable, enzymatically active, activated protein C upon resuspension because of reduced autodegradation. The present invention has particularly reduced levels of des(1–9) aPC and des(1–10) aPC. Generally, the levels of des(1–9) and des(1–10) aPC are less than 10% of the autodegradation product. Preferably, the levels of des (1–9) and des(1–10) aPC are less than 8% of the autodegradation product. Still more preferably, the levels of des (1–9) and des(1–10) aPC are less than 5% and most preferably less than 3% of the autodegradation product. This stability is obtained through careful control of the processing conditions and by the addition of sucrose, trehalose, raffinose, or mannitol. Interestingly, other bulking agents such as hydroxyethyl starch and glycine do not offer the necessary stability or pharmaceutical elegance.

The bulking agents of the present invention provide a pharmaceutically elegant formulation which has a uniform appearance and is readily solubilized when resuspended with the appropriate solute. Upon reconstitution, the formulation is stable for up to 24 hours to 48 hours at room temperature. Resulting in stability previously unachievable.

Preferred bulking agents in the formulation of activated protein C are sucrose, trehalose and raffinose. More preferred bulking agents are sucrose and raffinose and the most preferred bulking agent is sucrose. The amount of bulking agent in the formulation is 1 part aPC to 1 to 10 parts bulking agent on a weight to weight basis. Moreover, the bulking agent concentration of the formulation is an important formulation variable of the freeze drying process. The optimum concentration of bulking agent is dependent on the amount of aPC and species of bulking agent selected. The preferred concentration of sucrose in the freezing solution is 10 to 40 mg/mL. A more preferred concentration of sucrose is 15 to 30 mg/mL. The most preferred concentration of sucrose in the freezing solution is 15 mg/mL in a formulation of aPC at 2.5 mg/mL. The most preferred concentration of sucrose in the freezing solution is 30 mg/mL in a formulation of aPC at 5.0 mg/mL. The presence of the claimed bulking agent in the formulation of activated protein C offers increased chemical and physical stability.

Prior to freeze drying and upon reconstitution, it is preferable to maintain the pH in the range of 5.5 to 6.5 to minimize solution state autodegradation. The preferred pH of the formulation is a pH between about pH 5.6 and about pH 6.4. More preferred is a pH between about 5.7 to about 6.3. Even more preferred is a pH between about 5.8 to about 6.2. Still even more preferred is a pH between about 5.9 to about 6.1. The most preferred pH is about pH 6.0.

To maintain effective pH control, the aPC solution should contain a pharmaceutically acceptable buffer. Accordingly, upon freeze-drying, the formulation optionally and preferably comprises a pharmaceutically acceptable buffer. Representative buffer systems include Tris-acetate, sodium citrate, and sodium phosphate. More preferred buffer systems include sodium citrate and sodium phosphate. The most preferred buffer is sodium citrate. The preferred molarity of the buffer system is 10 mM to 50 mM. A more preferred molarity of the buffer system is 10 mM to 20 mM. The most preferred molarity is 40 mM. The skilled artisan will recognize that many other buffer systems are available which also can be used in the formulations of the present invention.

Similarly, during freeze drying and upon reconstitution, the ionic strength is a critical variable to ensure solution state stability. The ionic strength is generally determined by the salt concentration of the solution. Pharmaceutically acceptable salts typically used to generate ionic strength include but are not limited to potassium chloride (KCl) and sodium chloride (NaCl). The preferred salt in the present invention is sodium chloride. During freeze-drying, the salt concentration must be high enough to cause the salt to crystallize during the freezing step of the freeze-drying cycle. Preferably, the sodium chloride concentration is greater than 150 mM. More preferably, the sodium chloride concentration in the freezing solution is between 150 mM to 1000 mM. For a formulation containing 2.5 mg/mL aPC, the more preferable sodium chloride concentration in the freezing solution is between 150 mM to 650 mM. Even more preferably the sodium chloride concentration in the freezing solution is between 250 mM to 450 mM. Still even more preferably the sodium chloride concentration in the freezing solution is between 300 mM to 400 mM. The most preferable sodium chloride concentration in the freezing solution is 325 mM for a formulation containing 2.5 mg/mL aPC.

Similarly, for a formulation containing 5.0 mg/mL aPC, the more preferable sodium chloride concentration in the freezing solution is between 150 mM to 1000 mM. Even more preferably the sodium chloride concentration in the freezing solution is between 250 mM to 750 mM. Still even more preferably the sodium chloride concentration in the freezing solution is between 400 mM to 700 mM. The most preferable sodium chloride concentration in the freezing solution is 650 mM for a formulation containing 5.0 mg/mL aPC.

The ratio of aPC:salt:bulking agent (w:w:w) is an important factor in a formulation suitable for the freeze drying process. The ratio varies depending on the concentration of aPC, salt selection and concentration and bulking agent selection and concentration. One skilled in the art could readily identify the preferred ratio of aPC:salt:bulking agent by techniques appreciated in the art and described, for example, in Example 1. Particularly, a weight ratio of one part activated protein C to between about 7 to 8 parts salt to between about 5 to 7 parts bulking agent is preferred. More preferred is a weight ratio of one part activated protein C to between about 7.5 to about 8 parts salt to between about 5.5 to about 6.5 parts bulking agent. Most preferred is a ratio of about 1 part activated protein C to about 7.6 parts salt to about 6 parts bulking agent.

The preferred salt is sodium chloride at a concentration of 325 mM (for a formulation containing 2.5 mg/mL aPC) and 650 mM (for a formulation containing 5.0 mg/mL aPC) and at a ratio of about 1.3:1 with sucrose (w:w). This concentration is high enough to cause the salt to crystallize during the freezing process, most likely resulting in an amorphous mixture of aPC, sucrose, and citrate that can be lyophilized. Thus, the ionic strength of NaCl at the preferred concentrations of 325 mM and 650 mM convey a stability to the formulation during the freeze-drying process.

The present invention further provides a process for preparing a stable lyophilized formulation which comprises lyophilizing a solution comprising activated protein C and a bulking agent selected from the group consisting of mannitol, trehalose, raffinose, and sucrose, and mixtures thereof. The invention also provides a process for preparing a stable lyophilized formulation which comprises lyophilizing a solution comprising about 2.5 mg/mL activated protein C, about 15 mg/mL sucrose, about 19 mg/mL NaCl, and a sodium citrate buffer having a pH greater than 5.5 but less than 6.5. Furthermore, the present invention provides a process for preparing a stable lyophilized formulation which comprises lyophilizing a solution comprising about 5 mg/mL activated protein C, about 30 mg/mL sucrose, about 38 mg/mL NaCl, and a citrate buffer having a pH greater than 5.5 but less than 6.5.

The present invention provides a unit dosage form comprising a unit dosage receptacle containing a stable lyophilized formulation comprising activated protein C and a bulking agent selected from the group consisting of mannitol, trehalose, raffinose, and sucrose, and mixtures thereof. Furthermore, the present invention provides a method of treating disease states involving intravascular coagulation comprising the administration of said formulation.

The aPC is preferably administered parenterally to ensure its delivery into the bloodstream in an effective form by injecting the appropriate dose as continuous infusion for about one to about forty-eight hours. The amount of aPC administered is from about 0.01 mg/kg/hr to about 0.05 mg/kg/hr. Alternatively, the aPC will be administered by injecting a portion of the appropriate dose per hour as a bolus injection over a time from about 5 minutes to about 30 minutes, followed by continuous infusion of the appropriate dose for about twenty-three hours to about 47 hours which results in the appropriate dose administered over 24 hours to 48 hours.

The following examples will help describe how the invention is practiced and will illustrate the invention. The scope of the present invention is not to be construed as merely consisting of the following examples.

PREPARATION 1

Preparation of Human Protein C

Recombinant human protein C (r-hPC) was produced in Human Kidney 293 cells by techniques well known to the skilled artisan such as those set forth in Yan, U.S. Pat. No. 4,981,952, the entire teaching of which is herein incorporated by reference. The gene encoding human protein C is disclosed and claimed in Bang, et al., U.S. Pat. No. 4,775,624, the entire teaching of which is incorporated herein by reference. The plasmid used to express human protein C in 293 cells was plasmid pLPC which is disclosed in Bang, et al., U.S. Pat. No. 4,992,373, the entire teaching of which is incorporated herein by reference. The construction of plasmid pLPC is also described in European Patent Publication No. 0 445 939, and in Grinnell, et al., 1987, *Bio/Technology* 5:1189–1192, the teachings of which are also incorporated herein by reference. Briefly, the plasmid was transfected into 293 cells, then stable transformants were identified, subcultured and grown in serum-free media. After fermentation, cell-free medium was obtained by microfiltration.

The human protein C was separated from the culture fluid by an adaptation of the techniques of Yan, U.S. Pat. No. 4,981,952. The clarified medium was made 4 mM in EDTA before it was absorbed to an anion exchange resin (Fast-Flow Q, Pharmacia). After washing with 4 column volumes of 20 mM Tris, 200 mM NaCl, pH 7.4 and 2 column volumes of 20 mM Tris, 150 mM NaCl, pH 7.4, the bound recombinant human protein C zymogen was eluted with 20 mM Tris, 150 mM NaCl, 10 mM $CaCl_2$, pH 7.4. The eluted protein was greater than 95% pure after elution as judged by SDS-polyacrylamide gel electrophoresis.

Further purification of the protein was accomplished by making the protein 3 M in NaCl followed by adsorption to a hydrophobic interaction resin (Toyopearl Phenyl 650 M, TosoHaas) equilibrated in 20 mM Tris, 3 M NaCl, 10 mM $CaCl_2$, pH 7.4. After washing with 2 column volumes of equilibration buffer without $CaCl_2$, the recombinant human protein C was eluted with 20 mM Tris, pH 7.4.

The eluted protein was prepared for activation by removal of residual calcium. The recombinant human protein C was passed over a metal affinity column (Chelex-100, Bio-Rad) to remove calcium and again bound to an anion exchanger (Fast Flow Q, Pharmacia). Both of these columns were arranged in series and equilibrated in 20 mM Tris, 150 mM NaCl, 5 mM EDTA, pH 7.4. Following loading of the protein, the Chelex-100 column was washed with one column volume of the same buffer before disconnecting it from the series. The anion exchange column was washed with 3 column volumes of equilibration buffer before eluting the protein with 0.4 M NaCl, 20 mM Tris-acetate, pH 6.5. Protein concentrations of recombinant human protein C and recombinant activated protein C solutions were measured by UV 280 nm extinction $E^{0.1\%}$=1.81 or 1.85, respectively.

PREPARATION 2

Activation of Recombinant Human Protein C

Bovine thrombin was coupled to Activated CH-Sepharose 4B (Pharmacia) in the presence of 50 mM HEPES, pH 7.5 at 4° C. The coupling reaction was done on resin already packed into a column using approximately 5000 units thrombin/mL resin. The thrombin solution was circulated through the column for approximately 3 hours before adding 2-amino-ethanol (MEA) to a concentration of 0.6 mL/L of circulating solution. The MEA-containing solution was circulated for an additional 10–12 hours to assure complete blockage of the unreacted amines on the resin. Following blocking, the thrombin-coupled resin was washed with 10 column volumes of 1 M NaCl, 20 mM Tris, pH 6.5 to remove all non-specifically bound protein, and was used in activation reactions after equilibrating in activation buffer.

Purified r-hPC was made 5 mM in EDTA (to chelate any residual calcium) and diluted to a concentration of 2 mg/mL with 20 mM Tris, pH 7.4 or 20 mM Tris-acetate, pH 6.5. This material was passed through a thrombin column equilibrated at 37° C. with 50 mM NaCl and either 20 mM Tris pH 7.4 or 20 mM Tris-acetate pH 6.5. The flow rate was adjusted to allow for approximately 20 min. of contact time between the r-hPC and thrombin resin. The effluent was collected and immediately assayed for amidolytic activity. If the material did not have a specific activity (amidolytic) comparable to an established standard of aPC, it was recycled over the thrombin column to activate the r-hPC to completion. This was followed by 1:1 dilution of the material with 20 mM buffer as above, with a pH of either 7.4 or 6.5 to keep the aPC at lower concentrations while it awaited the next processing step.

Removal of leached thrombin from the aPC material was accomplished by binding the aPC to an anion exchange resin (Fast Flow Q, Pharmacia) equilibrated in activation buffer (either 20 mM Tris, pH 7.4 or 20 mM Tris-acetate, pH 6.5) with 150 mM NaCl. Thrombin does not interact with the anion exchange resin under these conditions, but passes through the column into the sample application effluent. Once the aPC is loaded onto the column, a 2–6 column volume wash with 20 mM equilibration buffer is done before eluting the bound aPC with a step elution using 0.4 M NaCl in either 5 mM Tris-acetate, pH 6.5 or 20 mM Tris, pH 7.4. Higher volume washes of the column facilitated more complete removal of the dodecapeptide. The material eluted from this column was stored either in a frozen solution (−20° C.) or as a lyophilized powder.

The anticoagulant activity of activated protein C was determined by measuring the prolongation of the clotting time in the activated partial thromboplastin time (APTT) clotting assay. A standard curve was prepared in dilution buffer (1 mg/mL radioimmunoassay grade bovine serum albumin [BSA], 20 mM Tris, pH 7.4, 150 mM NaCl, 0.02t $NaN_3$) ranging in protein C concentration from 125–1000 ng/mL, while samples were prepared at several dilutions in this concentration range. To each sample cuvette, 50 μL of cold horse plasma and 50 μL of reconstituted activated partial thromboplastin time reagent (APTT Reagent, Sigma) were added and incubated at 37° C. for 5 min. After incubation, 50 μL of the appropriate samples or standards were added to each cuvette. Dilution buffer was used in place of sample or standard to determine basal clotting time. The timer of the fibrometer (CoA Screener Hemostasis Analyzer, American Labor) was started immediately after the addition of 50 μL 37° C. 30 mM $CaCl_2$ to each sample or standard. Activated protein C concentration in samples are calculated from the linear regression equation of the standard curve. Clotting times reported here are the average of a minimum of three replicates, including standard curve samples.

EXAMPLE 1

Formulation of Activated Protein C

The human activated protein C was prepared as described in Preparations 1 and 2. The activated protein C formulations were analyzed for processing in a conventional freeze dryer. Freeze-Drying Microscopy and differential Scanning Calorimetry (DSC) were used to measure two parameters that determine if a formulation can be processed in a conventional freeze dryer. Freeze-Dry Microscopy is a useful technique in determining the collapse temperatures of the frozen solutions that are to be lyophilized. DSC is a useful technique in determining the glass-transition temperature (Tg') of the frozen solution. The collapse and glass-transition temperatures are especially helpful in predicting the upper temperature limits that can be safely used during the freeze-drying process. Results of Freeze-Drying Microscopy are complimentary to the glass-transition temperature of the Tg', values obtained by DSC. A collapse temperature above −40° C. is optimal for the sample to be processed in a conventional freeze-dryer.

TABLE 1

Freeze dry processing of aPC formulation matrices

| Formulation Matrix | | | |
|---|---|---|---|
| aPC Conc. | Sucrose Conc. | NaCl Conc. | Collapse Temperature |
| 2.5 mg/mL | 15 mg/mL | 50 mM | −59° C. |
| 2.5 mg/mL | 15 mg/mL | 150 mM | −60° C. |
| 2.5 mg/mL | 15 mg/mL | 325 mM | −37° C. |
| 5.0 mg/mL | 30 mg/mL | 50 mM | −50° C. to −45° C. |
| 5.0 mg/mL | 30 mg/mL | 150 mM | −60° C. to −55° C. |
| 5.0 mg/mL | 30 mg/mL | 325 mM | −64° C. |
| 5.0 mg/mL | 30 mg/mL | 650 mM | −32° C. to −28° C. |

The ratio of aPC to sucrose to sodium chloride (in 10 or 20 mM citrate buffer) is an important formulation variable affecting the collapse and glass-transition temperatures. To be processed in a conventional freeze-dryer, the sodium chloride concentration must be high enough (preferably 325 mM for 2.5 mg/mL aPC and 650 mM for 5 mg/mL aPC formulations) to cause the sodium chloride to crystallize-out during the freezing part of the freeze-drying process. Formulations of aPC can be processed in a conventional freeze dryer to produce lyophilized products consisting of 1 part aPC, 6 parts sucrose, and 7.6 parts odium chloride by weight.

EXAMPLE 2

Stability of aPC in Product Formulations Containing Different Bulking Agents

Formulations of aPC were prepared to investigate the effect of various bulking agents on the stability of the molecule. A total of six excipients were added to aPC in phosphate buffer containing no salt. These bulking agents are glycine, mannitol, sucrose, trehalose, raffinose, and hydroxyethyl starch (HES). The stability of aPC in the phosphate, no salt, no bulking agent formulation ("control") was compared to that in the bulking agent formulations. Samples were stored at 50° C., 40° C., and 25° C. for various lengths of time. Data from analyses of these samples were compared to the initial values (time=0). APTT potency, size exclusion-high performance liquid chromatography (SE-HPLC), SDS-PAGE, and protein content assays were used to evaluate the physical and chemical stability of the formulations.

Formulations of aPC were prepared by dissolving aPC in phosphate buffer to 5 mg/mL aPC. Bulking agents were added to portions of the aPC solution at a ratio of 6:1 (bulking agents to aPC), or 30 mg/mL. The samples were lyophilized to 5 mg aPC/vial.

The formulations were put on stability at 50° C. for 14 and 28 days; 40° C. for 28 days, 48 days and 6 months; and 25° C. for 6 and 12 months. For each time point, two vials of each formulation were analyzed independently as separate samples and data from these samples were compared to those from initial values (time=0). Analyses included aPC potency (APTT), SDS-PAGE, percent of aPC monomer, and protein content.

40° C./75% relative humidity, and then analyzed for possible degradation. The stability of aPC was also monitored after reconstitution with sterile water and storage for up to 72

|  | Vial | 25° C. | | | 50° C. | | | 40° C. | | | |
|---|---|---|---|---|---|---|---|---|---|---|---|
|  |  | Initial | 6 month | 12 month | Initial | 14 day | 28 day | Initial | 28 day | 84 day | 6 month |
| control | | | | | | | | | | | |
| APTT Potency | 1 | 321 | 294 | 236 | 321 | 248 | 248 | 321 | 248 | 221 | 215 |
| (U/mg) | 2 | 321 | 251 | 242 | 321 | 245 | 227 | 321 | 279 | 233 | 176 |
| Monomer | 1 | 99.3 | 98.3 | 96.5 | 99.3 | 97.5 | 97.0 | 99.3 | 97.7 | 96.2 | 95.1 |
| Content (%) | 2 | 99.2 | 95.8 | 96.4 | 99.2 | 97.3 | 97.1 | 99.2 | 97.7 | 96.1 | 95.4 |
| glycine | | | | | | | | | | | |
| APTT Potency | 1 | 282 | 233 | 142 | 282 | 164 | 97 | 282 | 191 | 155 | 158 |
| (U/mg) | 2 | 321 | 239 | 191 | 321 | 161 | 142 | 321 | 215 | 152 | 79 |
| Monomer | 1 | 99.1 | 98.4 | 93.3 | 99.1 | 97.4 | 97.2 | 99.1 | 97.8 | 96.4 | 95.8 |
| Content (%) | 2 | 99.1 | 98.4 | 96.3 | 99.1 | 97.3 | 97.1 | 99.1 | 97.7 | 96.4 | 95.7 |
| mannitol | | | | | | | | | | | |
| APTT Potency | 1 | 309 | 227 | 255 | 309 | 270 | 245 | 309 | 273 | 270 | 282 |
| (U/mg) | 2 | 321 | 321 | 267 | 321 | 239 | 242 | 321 | 300 | 251 | 191 |
| Monomer | 1 | 99.2 | 98.8 | 97.4 | 99.2 | 98.2 | 98.1 | 99.2 | 98.4 | 97.6 | 97.8 |
| Content (%) | 2 | 99.2 | 98.7 | 97.6 | 99.2 | 98.2 | 98.0 | 99.2 | 98.4 | 97.6 | 97.8 |
| sucrose | | | | | | | | | | | |
| APTT Potency | 1 | 327 | 300 | 288 | 327 | 300 | 288 | 327 | 267 | 306 | 285 |
| (U/mg) | 2 | 297 | 300 | 306 | 297 | 291 | 291 | 297 | 321 | 242 | 294 |
| Monomer | 1 | 99.2 | 99.0 | 98.5 | 99.2 | 98.7 | 98.9 | 99.2 | 98.8 | 98.5 | 98.9 |
| Content (%) | 2 | 99.2 | 99.0 | 98.5 | 99.2 | 98.7 | 98.9 | 99.2 | 98.8 | 98.5 | 98.9 |
| trehalose | | | | | | | | | | | |
| APTT Potency | 1 | 312 | 291 | 282 | 312 | 258 | 282 | 312 | 273 | 276 | 276 |
| (U/mg) | 2 | 309 | 315 | 282 | 309 | 270 | 215 | 309 | 303 | 245 | 255 |
| Monomer | 1 | 99.2 | 99.0 | 98.4 | 99.2 | 98.6 | 98.8 | 99.2 | 98.8 | 98.4 | 98.7 |
| Content (%) | 2 | 99.2 | 98.8 | 98.4 | 99.2 | 98.6 | 98.8 | 99.2 | 98.7 | 98.4 | 98.7 |
| raffinose | | | | | | | | | | | |
| APTT Potency | 1 | 321 | 270 | 255 | 321 | 261 | 258 | 321 | 276 | 273 | 279 |
| (U/mg) | 2 | 288 | 285 | 306 | 288 | 255 | 264 | 288 | 270 | 239 | 255 |
| Monomer | 1 | 99.1 | 99.0 | 97.0 | 99.1 | 98.6 | 98.7 | 99.1 | 98.7 | 98.4 | 98.6 |
| Content (%) | 2 | 99.1 | 99.0 | 98.2 | 99.1 | 98.6 | 98.7 | 99.1 | 98.7 | 98.4 | 98.6 |
| HES | | | | | | | | | | | |
| APTT Potency | 1 | 282 | 188 | 176 | 282 | 182 | 164 | 282 | 194 | 185 | 145 |
| (U/mg) | 2 | 285 | 245 | 215 | 285 | 188 | 161 | 285 | 176 | 152 | 103 |
| Monomer | 1 | 97.8 | 95.6 | 92.2 | 97.8 | 93.0 | 91.8 | 97.8 | 93.7 | 90.6 | 88.7 |
| Content (%) | 2 | 97.8 | 95.3 | 91.8 | 97.8 | 92.9 | 91.0 | 97.8 | 92.9 | 90.5 | 88.5 |

There were no significant changes in pH, color, package characteristics and physical appearance for any of the samples over the one year stability time period. When analyzed by the APTT and SE-HPLC procedures, the HES and glycine formulation had less physical stability (through aggregation) and chemical stability (potency) when compared to the control. The mannitol formulation offered slightly better physical and chemical stability than the control, and the remaining formulations, sucrose, trehalose and raffinose, all demonstrated even more superior physical and chemical stability when compared to the control. Therefore, mannitol sucrose, trehalose and raffinose, as bulking agents in aPC formulations, offer increased chemical and physical stability when compared to an aPC formulation without a bulking agent or those having glycine or HES.

EXAMPLE 3

Stability of Recombinant Human Activated Protein C

Two lots of a lyophilized formulation of recombinant human activated protein C (aPC) were stored for 1 month at 40° C./75% relative humidity, and then analyzed for possible degradation. The stability of aPC was also monitored after reconstitution with sterile water and storage for up to 72 hours at ambient temperature. The lyophilized aPC product consisted of 10 mg aPC, 60 mg sucrose, 76 mg sodium chloride, and 15.1 mg citrate per vial. The aPC in this formulation is stable in the dry state for at least one month when stored at 40° C./75% relative humidity, and in solution for 24 hours when stored at ambient temperature.

Both lots were prepared using the same unit formula of 10 mg aPC, 60 mg sucrose, 76 mg sodium chloride, and 15.1 mg citrate per vial. Both lyophilized lots of aPC were stored for 1 month at 40° C./75% relative humidity and the stability of aPC was monitored using the APTT potency assay, ion-pairing HPLC for quantitation of aPC peptides and mass spectrometry for quantitation of protein variant forms. One lot was also reconstituted with sterile water, to 1 mg/mL aPC, and held at ambient temperature. The stability of aPC in solution was monitored at the 0, 1, 4, 8, 24, 48 and 72 hour time points using the APTT and mass spectrometry methods.

There was no loss of aPC activity and an insignificant amount of structural degradation of the molecule after storage in the dry state for one month at 40° C./75% relative humidity. The aPC in this formulation is stable for up to 24 hours at 1 mg/mL after reconstitution.

We claim:

1. A lyophilized formulation comprising a weight to weight ratio of about 1 part activated protein C to between about 5 to 7 parts bulking agent.

2. The formulation of claim 1 wherein the bulking agent is selected from mannitol, trehalose, raffinose, and sucrose, and mixtures thereof.

3. The formulation of claim 2, further comprising a buffer selected from Tris-acetate, sodium citrate and sodium phosphate, or combinations thereof.

4. The formulation of claim 3, further comprising a buffer such that upon reconstitution the formulation has a pH of about 5.5 to about 6.5.

5. The formulation of claim 3, wherein the formulation contains less than 10% by weight of the autodegradation products des(1–9) and des(1–10).

6. The formulation of claim 1, wherein the ratio is about 1 mg of activated Protein C to between about 5 mg to about 7 mg of sucrose.

7. The formulation of claim 6, further comprising a buffer selected from Tris-acetate, sodium citrate and sodium phosphate, or combinations thereof.

8. The formulation of claim 7, further comprising a buffer such that upon reconstitution the formulation has a pH of about 5.5 to about 6.5.

9. The formulation of claim 7, wherein the formulation contains less than 10% by weight of the autodegradation products des(1–9) and des(1–10).

10. The formulation of claim 1, comprising about 5 mg of activated Protein C and about 25 to 35 mg of sucrose, in a unit dose receptacle.

11. The formulation of claim 10, further comprising a buffer selected from Tris-acetate, sodium citrate and sodium phosphate, or combinations thereof.

12. The formulation of claim 11, further comprising a buffer such that reconstitution results in a formulation having a pH of about 5.5 to about 6.5.

13. The formulation of claim 12, wherein the formulation contains less than 10% by weight of the autodegradation products des (1–9) and des(1–10).

14. The formulation of claim 10, wherein the formulation contains less than 10% by weight of the autodegradation products des (1–9) and des(1–10).

15. The formulation of claim 1, comprising about 10 mg of activated Protein C and between about 50 to 70 mg of sucrose, in a unit dose receptacle.

16. The formulation of claim 15, further comprising a buffer selected from Tris-acetate, sodium citrate and sodium phosphate, or combinations thereof.

17. A formulation comprising a weight to weight ratio of about 1 part activated protein C to between about 5.5 to 6.5 parts bulking agent.

18. The formulation of claim 17 wherein the bulking agent is selected from mannitol, trehalose, raffinose, and sucrose, and mixtures thereof.

19. The formulation of claim 18, further comprising a buffer selected from Tris-acetate, sodium citrate and sodium phosphate, or combinations thereof.

20. The formulation of claim 19, further comprising a buffer such that upon reconstitution the formulation has a pH of about 5.5 to about 6.5.

21. The formulation of claim 17, wherein the ratio is about 1 mg of activated Protein C to between about 5.5 mg to 6.5 mg of sucrose.

22. The formulation of claim 21, further comprising a buffer selected from Tris-acetate, sodium citrate and sodium phosphate, or combinations thereof.

23. The formulation of claim 22, further comprising a buffer such that upon reconstitution the formulation has a pH of about 5.5 to about 6.5.

24. The formulation of claim 17, comprising about 5 mg of activated Protein C and about 27.5 to 32.5 mg of sucrose, in a unit dose receptacle.

25. The formulation of claim 24, further comprising a buffer selected from Tris-acetate, sodium citrate and sodium phosphate, or combinations thereof.

26. The formulation of claim 25, further comprising a buffer such that reconstitution results in a formulation having a pH of about 5.5 to about 6.5.

27. The formulation of claim 24, wherein the formulation contains less than 10% by weight of the autodegradation products des(1–9) and des(1–10).

28. The formulation of claim 17, comprising about 10 mg of activated Protein C and between about 55 mg to 65 mg of sucrose, in a unit dose receptacle.

29. The formulation of claim 28, further comprising a buffer selected from Tris-acetate, sodium citrate and sodium phosphate, or combinations thereof.

30. A formulation comprising a weight to weight ratio of about 1 part activated protein C and about 6 parts bulking agent.

31. The formulation of claim 30 wherein the bulking agent is selected from mannitol, trehalose, raffinose, and sucrose, and mixtures thereof.

32. The formulation of claim 31, further comprising a buffer selected from Tris-acetate, sodium citrate and sodium phosphate, or combinations thereof.

33. The formulation of claim 32, further comprising a buffer such that upon reconstitution the formulation has a pH of about 5.5 to about 6.5.

34. The formulation of claim 30, wherein the ratio is about 1 mg of activated Protein C to about 6 mg of sucrose.

35. The formulation of claim 34, further comprising a buffer selected from Tris-acetate, sodium citrate and sodium phosphate, or combinations thereof.

36. The formulation of claim 35, further comprising a buffer such that upon reconstitution the formulation has a pH of about 5.5 to about 6.5.

37. The formulation of claim 30, comprising about 5 mg of activated Protein C and about 30 mg of sucrose, in a unit dose receptacle.

38. The formulation of claim 37, further comprising a buffer selected from Tris-acetate, sodium citrate and sodium phosphate, or combinations thereof.

39. The formulation of claim 38, further comprising a buffer such that reconstitution results in a formulation having a pH of about 5.5 to about 6.5.

40. The formulation of claim 30, comprising about 10 mg of activated Protein C and about 60 mg of sucrose, in a unit dose receptacle.

41. The formulation of claim 40, further comprising a buffer selected from Tris-acetate, sodium citrate and sodium phosphate, or combinations thereof.

42. The formulation according to any of claim 35 further comprising a salt.

43. The formulation of claim 42, wherein the salt is selected from sodium chloride and potassium chloride.

* * * * *

UNITED STATES PATENT AND TRADEMARK OFFICE
CERTIFICATE OF CORRECTION

PATENT NO.    : 6,395,270 B1  
DATED         : May 28, 2002  
INVENTOR(S)   : Andrew David Carlson and Theodore Arsay Sheliga It is certified that error appears in the above-identified patent and that said Letters Patent is hereby corrected as shown below:

<u>Column 12,</u>
Lines 60-61, Claim 42 should read as follows:

42.    The formulation according to any of claims 1-8, 10-12, 15-26, or 28-41, further comprising a salt.

Signed and Sealed this

Fifteenth Day of April, 2003

JAMES E. ROGAN  
*Director of the United States Patent and Trademark Office*